United States Patent [19]
Veriac

[11] Patent Number: 5,994,138
[45] Date of Patent: Nov. 30, 1999

[54] STAINING REAGENT FOR THE DETERMINATION OF BLOOD CELLS

[75] Inventor: Sylvie Veriac, Montpellier, France

[73] Assignee: ABX, Montpellier Cedex, France

[21] Appl. No.: 09/008,498

[22] Filed: Jan. 16, 1998

[30] Foreign Application Priority Data

Jan. 31, 1997 [FR] France ................................. 97 01090

[51] Int. Cl.⁶ .................................................. G01N 31/00
[52] U.S. Cl. .................................. 436/10; 436/8; 436/17; 436/63; 436/172; 252/408.1
[58] Field of Search ................................ 436/8, 10, 16, 436/17, 18, 63, 172; 252/408.1

[56] References Cited

U.S. PATENT DOCUMENTS

| | | | |
|---|---|---|---|
| 4,670,402 | 6/1987 | Flegler ....................................... | 436/66 |
| 4,883,867 | 11/1989 | Lee et al. ................................. | 436/63 X |
| 5,075,556 | 12/1991 | Fan et al. ................................. | 436/63 X |
| 5,077,056 | 12/1991 | Bally et al. ............................... | 436/829 X |
| 5,174,872 | 12/1992 | Scott ........................................ | 436/18 X |
| 5,411,891 | 5/1995 | Fan et al. ................................. | 436/63 |
| 5,438,003 | 8/1995 | Colella et al. ............................ | 436/63 |
| 5,633,167 | 5/1997 | Fan et al. ................................. | 436/17 |
| 5,658,151 | 8/1997 | Yue .......................................... | 435/34 |
| 5,691,204 | 11/1997 | Kim et al. ................................ | 436/63 |
| 5,733,784 | 3/1998 | Studholme et al. ...................... | 436/63 |

FOREIGN PATENT DOCUMENTS

| | | |
|---|---|---|
| 226 272 A1 | 6/1987 | European Pat. Off. . |
| 0 430 719 A2 | 5/1991 | European Pat. Off. . |
| 0 545 315 A1 | 6/1993 | European Pat. Off. . |

OTHER PUBLICATIONS

Derwent Publications Ltd., GB, Class B04, AN 86–142078, Section Ch, Week 8622, XP002044489 & JP 61 079 163A (TOA IYO DENSHI KK), 1986.

*Primary Examiner*—Maureen M. Wallenhorst
*Attorney, Agent, or Firm*—Pollock, Vande Sande & Amernick

[57] ABSTRACT

The invention concerns a staining reagent for the determination of blood cells, in particular reticulocytes, which contains a stain capable of labelling cells after incubation, as well as an additive which is able to encourage penetration of the stain into the cells, this additive being chosen from an ionophoric compound, a detergent and mixtures thereof.

17 Claims, 4 Drawing Sheets

STAINING REAGENT FOR THE DETERMINATION OF BLOOD CELLS

FIELD OF THE INVENTION

The invention concerns biological analyses and, in particular, blood analyses.

More particularly, the present invention concerns a staining reagent for the determination of blood cells, in particular reticulocytes, of the type containing a stain capable of labelling cells after incubation.

BACKGROUND OF THE INVENTION

Very different staining reagents of the type of the present invention are already known which enable blood cells to be identified and characterized by a stain which enables the cells to be labelled or stained after incubation under chosen time and temperature conditions.

Such reagents generally make use of a fluorescent stain or a non-fluorescent stain which, after incubation, enables the stained cells to be counted. This counting may be carried out with manual staining under a microscope, with external staining or with staining using an automated apparatus.

Automated counting is generally carried out by a so-called flow cytometry technique which proves to be more reliable and more rapid than manual counting.

Various stains are already known which are used for the determination of blood cells, in particular reticulocytes, and which may be used for manual or automated counting.

these fluorescent or non-fluorescent stains include pyronine Y, acridine orange, thioflavine T, thiazole orange, new methylene blue, brilliant cresyl blue etc.

Examples of staining reagents are described in particular in the following patent publications: CA 2 024 166, U.S. Pat. No. 5 501 954, U.S. Pat. No. 4 325 706, U.S. Pat. No. 5 438 003, U.S. Pat. No. 5 075 556, U.S. Pat. No. 4 996 040, U.S. Pat. No. 4 883 867, EP 0 545 314, EP 0 545 315, EP 0 430 719, EP 0 215 461, EP 0 226 272 and EP 0 114 462.

In the particular case of the determination of reticulocytes, which are precursors of erythrocytes or mature red corpuscles, the stain serves to color or label the residual RNA contained in the cell.

One of the disadvantages of known staining reagents is that they require a long incubation time, which makes them difficult to use not only in manual techniques but especially in automated techniques.

In particular, thiazole orange requires an incubation time of the order of 30 minutes at room temperature when it is reacted with 5 microlitres of blood.

This incubation time is much too long to enable the process to be completely automated.

SUMMARY OF THE INVENTION

The object of the invention is, in particular, to overcome the aforementioned disadvantages.

One aim of the invention is in particular to produce a staining reagent for the determination of blood cells, in particular reticulocytes, which enables the cells to be labelled after a much shorter incubation time than incubation times possible with known reagents.

One aim of the invention is in particular to produce such a staining reagent which enables the incubation time to be reduced from a few minutes to a few seconds.

To this end, the invention provides a staining reagent of the type defined in the introduction, which additionally includes an additive which is able to encourage penetration of the stain into the cell, this additive being chosen from an ionophoric compound, a detergent and mixtures thereof.

Thus, the staining reagent of the invention combines a stain and a special additive which encourages the incorporation of the stain in the cell and, consequently, considerably reduces the incubation time required for the reaction between the stain and the cell.

Within the context of the invention, preference is especially given to the use of an ionophoric compound, namely a compound capable of increasing the permeability of the cellular membrane and of amplifying trans-membranous exchanges.

These ionophores are molecules with a hydrophobic character which increase the permeability of the cellular membrane to certain ions with a variable specificity.

These ionophores are either mobile carriers, or molecules forming trans-membranous channels. They mask the charge on the ion of the stain, facilitating its penetration into the lipidic bilayer of the membrane.

The additive of the invention may also be chosen from a detergent which also encourages penetration of the stain by increasing the permeability of the membrane. The detergent disorganizes the proteinic structures of the membrane and encourages their destabilization, which contributes to a better incorporation of the stain.

The additive of the invention may alternatively be a mixture of an ionophoric compound and a detergent.

The ionophoric compound of the invention may in particular be a protonophore or an antibiotic.

DETAILED DESCRIPTION OF THE PREFERRED EMBODIMENTS

Figure 1A:
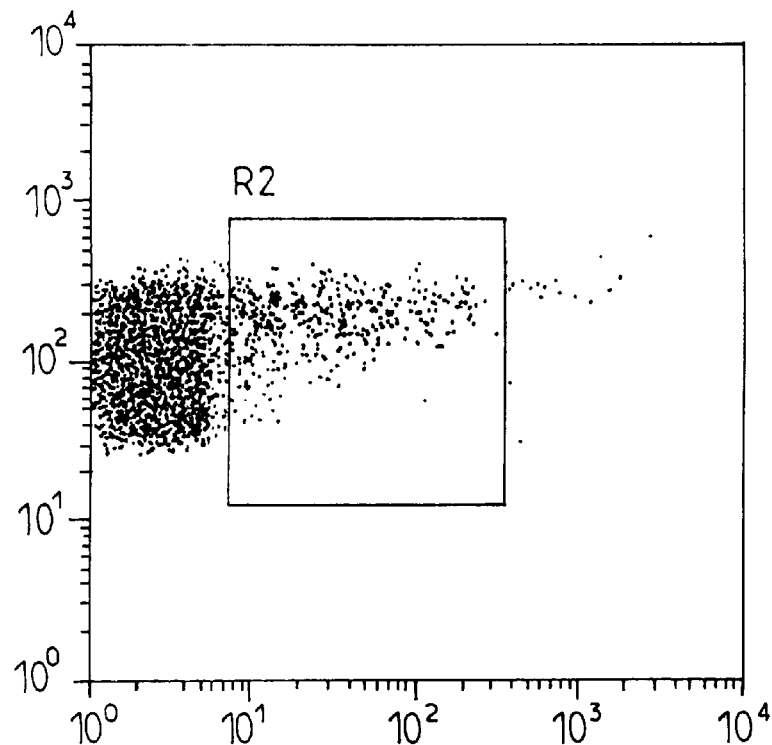
FIG. 1A and 1B show images obtained on a FACSAN flow cytometer (registered trademark of Becton Dickinson) using thiazole orange stain.

Non-limiting examples of ionophoric compounds suitable for putting the invention into practice are as follows:

Monensin, or 2-[5-ethyltetrahydro-5-[tetrahydro-3-methyl-5-[tetrahydro-6-hydroxy-6-(hydroxymethyl)-3,5-dimethyl-2H-pyran-2-yl]-2-furyl]-2-furyl]-9-hydroxy-$\beta$-methoxy-$\alpha,\gamma$, 2,8-tetramethyl-1,6-dioxaspiro[4,5]decane-7-butyric acid (antibiotic polyether with the empirical formula: $C_{36}H_{62}O_{11}$);

Nonactin, or 2,5,11,14,20,23,29,32-octamethyl-4,13,22,31,37, 38,39,40-octaoxapentacyclo[32.2.1.1$^{7,10}$.1$^{16,19}$.1$^{25,28}$]-tetracontane-3,12,21,30-tetrone (antibiotic macrotetrolide with the empirical formula: $C_{40}H_{64}O_{12}$);

3,5-di-tert-butyl-4-hydroxy-benzylidenemalononitrile;

carbonylcyanide m-chlorophenylhydrazone;

carbonylcyanide p-trifluoromethoxyphenylhydrazone;

tetrachlorosalicylanilide;

4,5,6,7-tetrachloro-2-trifluoromethylbenzimidazole;

pentachlorophenol;

2,4-dinitrophenol;

Valinomycin (antibiotic cyclododecadepsi-peptide with the formula $C_{54}H_{90}N_6O_{18}$);

Salinomycin (antibiotic polyether with the formula: $C_{42}H_{70}O_{11}$)

Gramicidin(S) (polypeptide with the formula: $C_{60}H_{92}N_{12}O_{10}$).

The detergent that can be used in the staining reagent of the invention is preferably of the non-ionic type or zwitterionic type.

As non-limiting examples of detergents suitable for putting the invention into practice, mention may be made of:

propane sulphonates, in particular 3-[(3-cholamidopropyl)-dimethylammonio]-1-propane-sulphonate;

cholamides, in particular N,N-bis[3-D-gluconamidopropyl]-cholamide;

sulphobetaines;

alkyl glucosides and alkyl maltosides;

polyoxyethylene ethers;

polyoxyethylene sorbitans;

polyglycol ethers.

The stain that can be used in the staining reagent of the invention is a marker able to reveal by staining intracellular compounds such as, for example, nucleic acids of the cell, in particular RNA.

Although a fluorescent stain is preferred, and in particular a fluorescent stain for reticulocytes, the use of non-fluorescent stains also falls within the scope of the invention.

When a fluorescent stain is used, the stain is advantageously one which can be excited at a wavelength of between 0.1 nm and 1 mm.

Preferably, a stain is used which can be excited in blue light, in particular at a wavelength of 488 nm.

As non-limiting examples of stains which can be used for putting the invention into practice, mention may be made of:

3,3'-dimethyloxacarbocyanine iodide (or 3-methyl-2-[3-(3-methyl-2(3H)-benzoxazolylidene)-1-propenyl] benzoxazolium iodide;

thiazole orange or 1-methyl-4-[(3-methyl-2-(3H)-benzothiazolylidene)methyl]quinolinium p-tosylate;

quinolinium, 4-[(3-methyl-2-(3H)-benzothiazolylidene) methyl]-1-[3-(trimethylammonio)propyl]diiodide, (marketed under the registered trademark TO-PRO 1 by Molecular Probes);

styryls, in particular styryl 7;

new methylene blue brilliant cresyl blue.

When this known stain is combined with an ionophoric compound and/or a detergent in the chosen proportions, it rapidly crosses the cell membrane, which enables the incubation time to be appreciably reduced and to be generally brought down to a value of a few tens of seconds.

Thus, in the case of thiazole orange, the incubation time may be brought down to a value of the order of 25 seconds, instead of 30 minutes at room temperature, when the stain is used on its own.

The staining reagent of the invention may include compounds or substances other than the stain and the additive previously mentioned.

Thus, the staining reagent may additionally include an organic solvent, in particular an alcohol such as methanol, which assists in dissolving the stain, but also assists in solubilizing the membranous lipids of the cell.

As an alternative or as a complement, the staining reagent may additionally include a salt, for example one based on sodium or potassium.

It was in fact found that a concentration of salts induced a so-called "ionic" force which, if it was sufficiently high, could destabilize the cell membranes by modifying the bonds between the membranous constituents. In addition, the salt could act on the volume of the cells.

Other compounds which can participate in the reagent of the invention include a chelating agent, in particular EDTA, a preservative and a buffer system for maintaining the pH between 5 and 11.

The typical reagent of the invention is a staining or labelling solution which contains:

a stain at a concentration of between 0.1 $\mu$M and 0.5 M at least one additive chosen from those below

| Compounds | Concentrations |
|---|---|
| Ionophore | 0–1M |
| Detergent | 0–20% | one or more of the compounds listed below:

| Compounds | Concentrations |
|---|---|
| Salts (NaCl/KCl) | 0–1M |
| Chelating agent (EDTA) | 0–100 mM |
| Solvent | 0–15% |
| Preservative | 0–1% | an organic or inorganic buffer system maintaining the pH between 5 and 11.

An example of a staining reagent according to the invention is as follows:

| Compound | Concentrations |
|---|---|
| Thiazole orange | 2 $\mu$M |
| Valinomycin | 1 $\mu$M |
| Polyglycol ether | 0.0003% |
| NaCl | 155 mM |
| EDTA | 2 mM |
| Methanol | 1.5% |

The buffer system used is a phosphate buffer adjusting the pH of the stain solution to a neutral value.

The invention will now be explained with reference to the accompanying drawings, which represent the images obtained on a flow cytometer, which each time makes a comparison between the image obtained with a reference dye and the image obtained with a staining reagent according to the invention.

These images represent fluorescence (X axis) and diffraction (Y axis). Three populations will be found in each of these figures from left to right respectively: a red corpuscle population (appearing in the form of a cloud), a reticulocyte population (framed part) and a leucocyte population (scattered cloud).

Figure 1B:
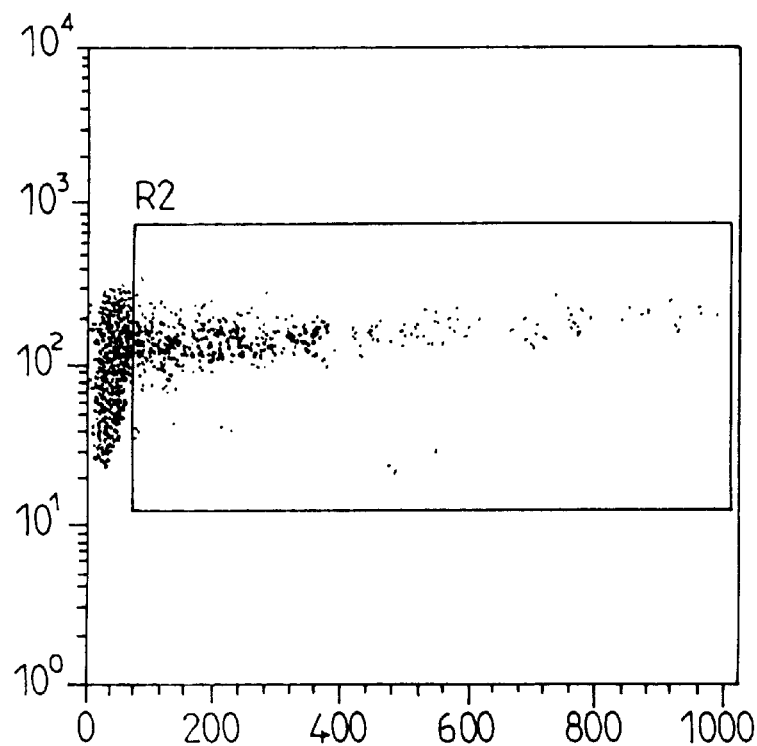

FIGS. 1A and 1B show the images obtained on a FAC-SCAN flow cytometer (registered trademark of Becton Dickinson) using thiazole orange as the stain.

FIG. 1A shows the image obtained with the reference stain. The incubation time required was 30 minutes at room temperature. The reticulocyte count was 4.55%.

FIG. 1B shows the image obtained with the staining reagent of the invention, which included thiazole orange in the presence of ionophore. The incubation time required was 25 seconds at 35° C., the reticulocyte count being 4.89%.

Figure 2A:
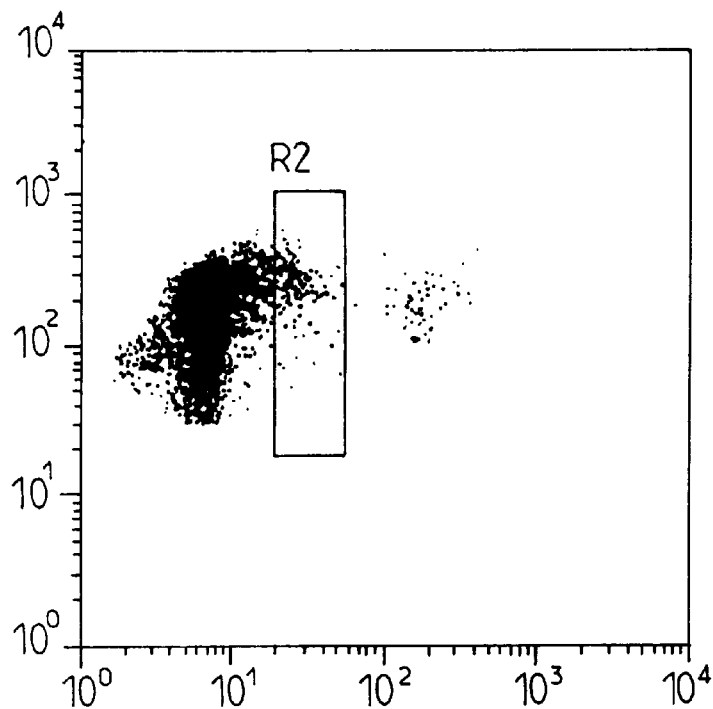
FIGS. 2A and 2B show images obtained on a FACSAN flow cytometer (registered trademark of Becton Dickinson) using a staining reagent according to the present invention.
Figure 2B:
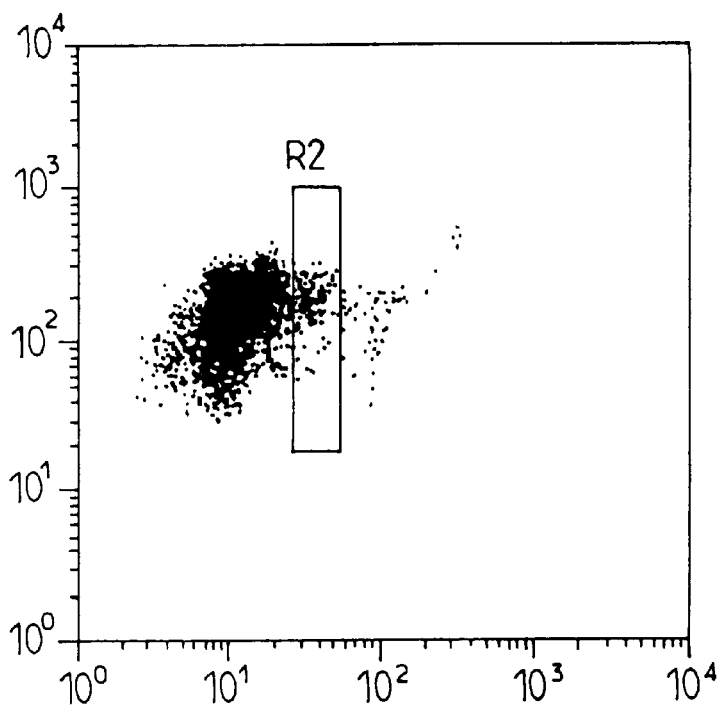

FIGS. 2A and 2B are the images obtained with a FACS-CAN flow cytometer using a staining reagent according to the invention, which included 3,3'-dimethylcarbocyanine iodide as the stain, in the presence of an ionophore and a detergent.

The two staining operations were carried out at 35° C. An equivalent result was obtained in 5 minutes for the reference stain (FIG. 2A) and in 30 seconds for the reagent according to the invention (FIG. 2B).

The reticulocyte count in the images of FIGS. 2A and 2B are 1.5% and 1.3% respectively.

Figure 3A:
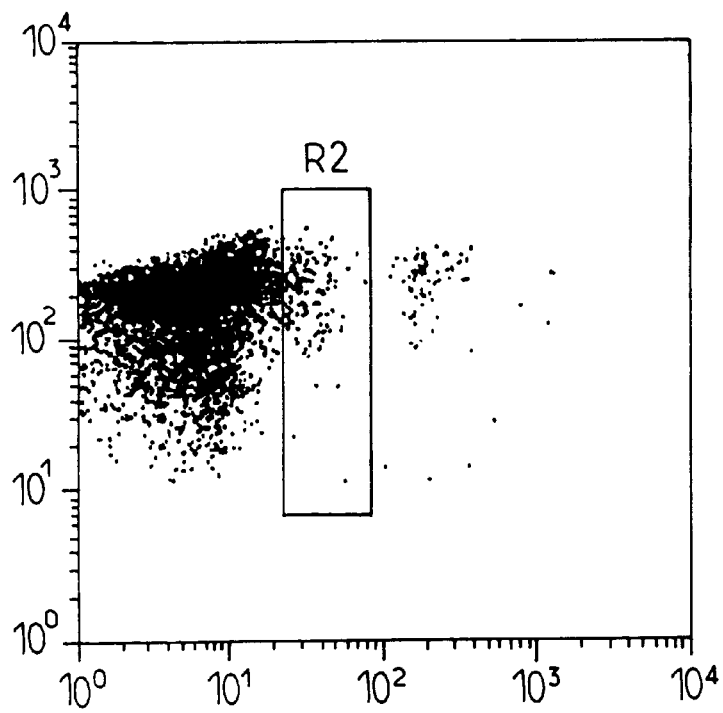
FIGS. 3A and 3B show images obtained on a FACSAN flow cytometer (registered trademark of Becton Dickinson) using TO-PRO 1 (registered trademark of Molecular Probes) stain.
Figure 3B:
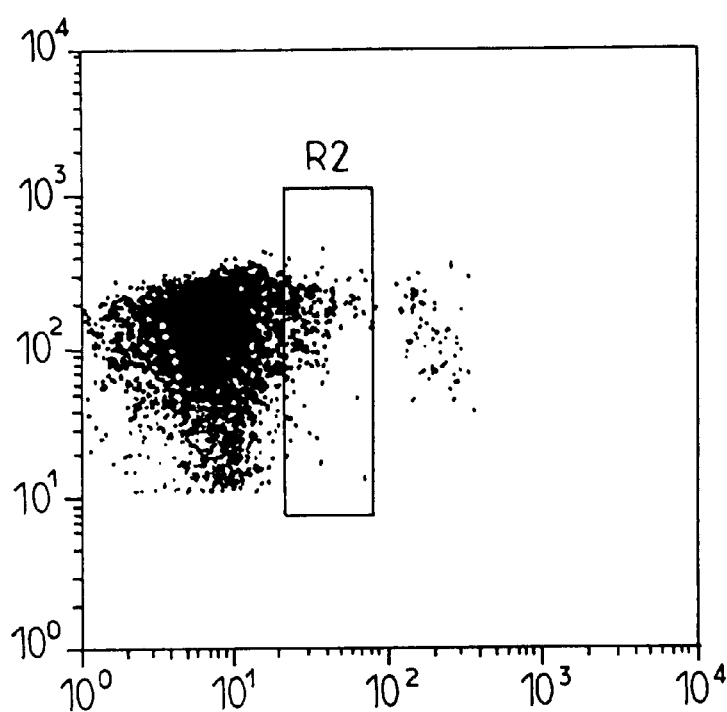

FIGS. 3A and 3B are the images obtained on a FACSCAN flow cytometer with the stain TO-PRO 1 (registered trademark of Molecular Probes), under irradiation with blue light.

In the case of FIG. 3A (reference stain), the incubation time was 60 minutes and the raticulocyte count was 2.22.

In the case of FIG. 3B (stain in the presence of ionophore), the incubation time was 5 minutes and the reticulocyte count was 2.14%

Figure 4A:
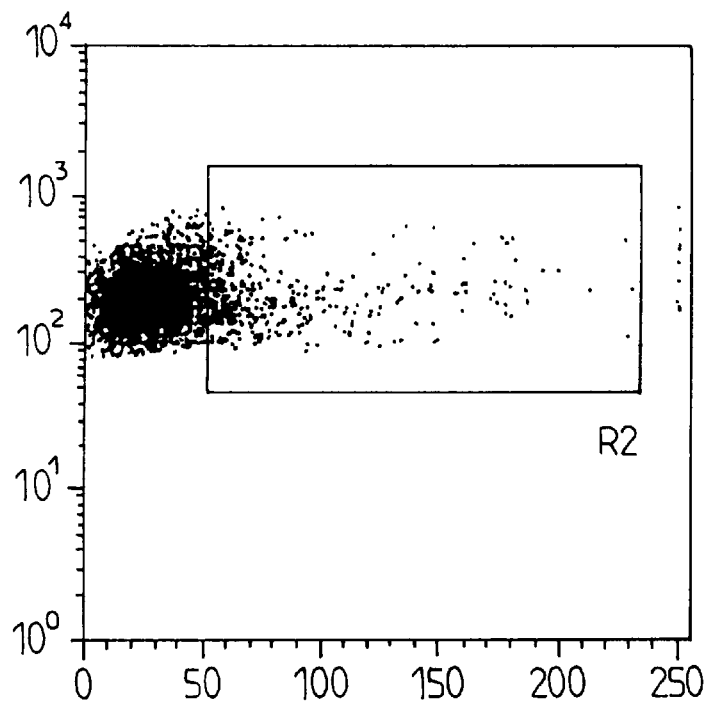
FIGS. 4A and 4B show images obtained on a FACSTAR flow cytometer (registered trademark of Becton Dickinson) using TO-PRO 3 (registered trademark of Molecular Probes) stain.
Figure 4B:
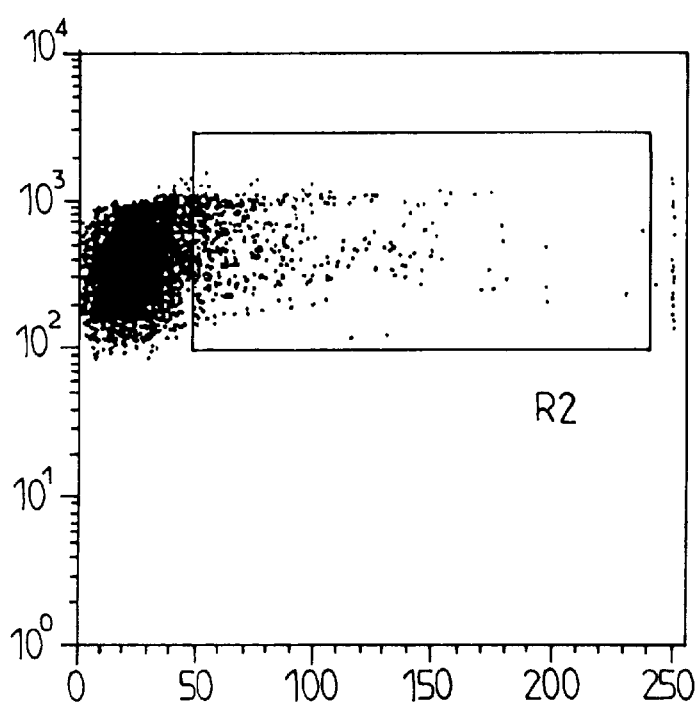

FIGS. 4A and 4B show the images obtained on a FAC-STAR flow cytometer (registered trademark of Becton Dickinson) with a stain of the TO-PRO 3 type (registered trademark of Molecular Probes), under irradiation with red light.

In the case of FIG. 4A (reference stain), the incubation time was 30 minutes and the reticulocyte count was 4.1%.

In the case of FIG. 4B, the incubation time was 2 minutes and the reticulocyte count was 4.90%.

The preceding images show that the use of a staining reagent according to the invention enables the incubation time to be significantly reduced compared with the use of a reference stain.

What is claimed is:

1. A staining reagent for determining blood cells, comprising:
   a stain capable of labelling cells after incubation; and
   an additive capable of encouraging penetration of the stain into the cells, the additive being selected from the group consisting of an ionophoric compound and a mixture of an ionophoric compound with a detergent.

2. The staining reagent according to claim 1, wherein the stain is of the fluorescent type.

3. The staining reagent according to claim 1, wherein the stain can be excited at a wavelength of between 0.1 nm and 1 mm.

4. The staining reagent according to claim 1, wherein the stain can be excited in blue light.

5. The staining reagent according to claim 1, wherein the reagent additionally includes at least one compound selected from the group consisting of:
   a salt,
   a chelating agent,
   a solvent,
   a preservative and
   a buffer system maintaining the pH at between 5 and 11.

6. The staining reagent according to claim 5, wherein the at least one compound includes a salt selected from the group consisting of sodium salts and potassium salts.

7. The staining reagent according to claim 5, wherein the at least one compound includes EDTA.

8. The staining reagent according to claim 5, wherein the at least one compound includes an alcohol.

9. The staining reagent according to claim 1, wherein the staining reagent determines reticulocytes.

10. The staining reagent according to claim 1, wherein the stain can be excited in light having a wavelength of 488 nm.

11. The staining reagent according to claim 1, wherein the stain in styryl 7.

12. The staining reagent according to claim 1, wherein the ionophoric compound is a protonophore or an antibiotic selected from the group consisting of:

monensin, or 2-[5-ethyltetrahydro-5-[tetrahydro-3-methyl-5-[tetrahydro-6-hydroxy-6-(hydroxymethyl)-3,5-dimethyl-2H-pyran-2-yl]-2-furyl]-2-furyl]-9-hydroxy-β-methoxy-α,γ, 2,8-tetramethyl-1,6-dioxaspiro[4,5]decane-7-butyric acid;

nonactin, or 2,5,11,14, 20,23,29,32-octamethyl-4,13,22,31,37,38,39,40-octaoxapentacyclo[32.2.1.1$^{7,10}$. 1$^{16,19}$.1$^{25,28}$]tetracontane-3,12,21,30-tetrone;

3,5-di-tert-butyl-4-hydroxy-benzylidenemalononitrile;

carbonylcyanide m-chlorophenylhydrazone;

carbonylcyanide p-trifluoromethoxyphenylhydrazone;

tetrachlorosalicylanilide;

4,5,6,7-tetrachloro-2-trifluoromethylbenzimidazole;

pentrachorophenol;

2,4-dinitrophenol;

Valinomycin;

Salinomycin; and

Gramicidine (S).

13. The staining reagent according to claim 1, wherein the detergent is of the non-ionic or zwitterionic type and is selected from the group consisting of:

propane sulphonates;

cholamides;

sulphobetaines;

alkyl glucosides and alkyl maltosides;

polyoxyethylene ethers;

polyoxyethylene sorbitans; and polyglycol ethers.

14. The staining reagent according to claim 13, wherein the detergent is 3-[(3-cholamidopropyl)-dimethylammonio]-1-propane-sulphonate.

15. The staining reagent according to claim 13, wherein the detergent is N,N-bis[3-D-gluconamidopropyl]-cholamide.

16. The staining reagent according to claim 1, wherein the stain is selected from the group consisting of:

3,3'-dimethyloxacarbocyanine iodide (or 3-methyl-2-[3-(3-methyl-2(3H)-benzoxazolylidene)-1-propenyl] benzoxazolium iodide;

thiazole orange or 1-methyl-4-[3-methyl-2-(3H)-benzothiazolylidene)methyl]quinolinium p-tosylate);

quinolinium or 4-[(3-methyl-2-(3H)-benzothiazolylidene) methyl]-1-[3-(trimethylammonio)propyl]diiodide;

styryls;

new methylene blue; and brilliant cresyl blue.

17. The staining reagent according to claim 1, wherein the reagent has the following composition:
   a stain at a concentration of between 0.1 μM and 0.5 M;
   at least one additive selected from the group consisting of an ionophore at a concentration of 0–1 M and a mixture of an ionophore at a concentration of 0–1 M with a detergent at a concentration of 0–20% weight per unit volume;

one or more of the compounds selected from the group consisting of NuCl or KCl salts at a concentration of 0–1 M, a chelating agent at a concentration of 0–100 mM, a solvent at a concentration of 0–15% weight per unit volume and a preservative at a concentration of 0–1% weight per unit volume; and an organic or inorganic buffer system maintaining the pH between 5 and 11.

* * * * *